United States Patent
Hutin et al.

(10) Patent No.: US 6,953,807 B2
(45) Date of Patent: Oct. 11, 2005

(54) 4-SUBSTITUTED-PICOLINIC ACID AMIDE DERIVATIVES USEFUL AS FUNGICIDES

(75) Inventors: Pierre Hutin, Lyons (FR); Benoît Muller, Lyons (FR); Christopher Richard Steele, Lyons (FR); Joseph Perez, Lyons (FR); Pierre Genix, Lyons (FR)

(73) Assignee: Bayer Cropscience S.A. (FR)

( * ) Notice: Subject to any disclaimer, the term of this patent is extended or adjusted under 35 U.S.C. 154(b) by 0 days.

(21) Appl. No.: 10/483,513

(22) PCT Filed: Jul. 5, 2002

(86) PCT No.: PCT/EP02/08665

§ 371 (c)(1),
(2), (4) Date: Mar. 22, 2004

(87) PCT Pub. No.: WO03/006456

PCT Pub. Date: Jan. 23, 2003

(65) Prior Publication Data

US 2004/0142977 A1 Jul. 22, 2004

(30) Foreign Application Priority Data

Jul. 11, 2001 (FR) .............................. 01 09195

(51) Int. Cl.⁷ ..................... C07D 401/04; A01N 43/40
(52) U.S. Cl. ................. 514/336; 546/268.1; 546/272.7; 546/276.4; 514/340; 514/341; 514/343
(58) Field of Search ................. 546/314, 268.1, 546/272.7, 276.4; 514/354, 336, 340, 341, 343

(56) References Cited

FOREIGN PATENT DOCUMENTS

| | | |
|---|---|---|
| WO | WO 01/05769 | 1/2001 |
| WO | WO 01/14339 | 3/2001 |
| WO | WO 01/49666 | 7/2001 |

OTHER PUBLICATIONS

Brunner, Henri et al.: "Asymetric catalysis. Part 117. Novel chiral oxazoline ligands for potential charge–transfer effects in the Rh(I)–catalyzed enantioselective hydrosilylation" European Journal of Inorganic Chemistry, No. 6, 1998, pp. 771–781, XP002216185 Wiley–VCH Verlag, Weinheim., DE ISSN: 1434–1948 compound 7.

Morkved, Eva H. et al.: "Potential acyl–transfer agents. Reactions of N–acyl–2–pyridinecarboxamides with nucleophiles" ACTA Chemica Scandinavica., vol. 36, No. 6—1982 pp. 381–388, XP00974283, Munksgaard, Copenhagen., DK, ISSN: 0904–213X, compounds 3f, 3g, 3h, 3j, 3k, 3m.

Morkved Eva H.: "Reactions of 4–(1–pyrrolidinyl)pyridine–2–carboxanilides with acyl halide to give acyl imidate hydrohalides" ACTA Chemica Scandinavica, Series B—Organic Chemistry and Biochemistry, vol. 33, No. 6,—1979 pp. 433–436, XP002216197, Copenhagen, DK, compounds 1a, 1b, 1d.

E.H. Morkved et al.: "Synthesis of some substituted picolinimidoyl chloride hydrochlorides", ACTA Chemica Scandinavica., vol. B32, No. 3, 1978, pp. 231–234, XP002216089, Munksgaard, Copenhagen, DK, ISSN: 0904–213X, compounds 1a, 1c, 1d, 1f, 1g, 1i.

*Primary Examiner*—Zinna Northington Davis
(74) *Attorney, Agent, or Firm*—Ostrolenk, Faber, Gerb & Soffen, LLP

(57) ABSTRACT

Compound of general formula (I) in which Y is chosen from the following groups $Y^1$ to $Y^3$ (I*), the other substituents being as defined in the description, process for preparing this compound, fungicidal composition comprising this compound, method for treating plants by applying this compound or composition.

13 Claims, No Drawings

4-SUBSTITUTED-PICOLINIC ACID AMIDE DERIVATIVES USEFUL AS FUNGICIDES

CROSS REFERENCE TO RELATED APPLICATION

The present application is a 35 U.S.C. § 371 national phase conversion of PCT/EP02/08665, filed Jul. 5, 2002, which claims priority of French Application No. 01/09195 filed Jul. 11, 2001.

The present invention relates to novel picolinic acid derivatives, the method for preparing them, their use as fungicides, particularly in the form of fungicidal compositions, and a method for controlling phytopathogenic fungi of crops using these compounds or these compositions.

Picolinic acid derivatives with fungicidal action are known in the literature. Thus, actimycin and some of its derivatives, which are described particularly in patent application WO-A-99/11127 and by Kuzo SHIBATA et al. (*The Journal of Antibiotics*, 51 (12), (1998), 1113–1116), are presented as being effective against phytopathogenic fungi of plants, with a good efficacy. These compounds, as well as those described in patent U.S. Pat. No. 3,228,950, do not have substituents in the 4-position of the pyridine nucleus.

Patent application WO-A-00/26191 presents picolinamide derivatives which are optionally substituted at the 4-position with the methoxy radical. Patent application WO-A-95/25723 proposes, for its part, 3-pyridylcarboxylic acid derivatives.

Amide derivatives of picolinic acid are also known from the publication of patent application JP-11228542. These derivatives are presented as having potential antifungal activities and low toxicity to be used in pharmaceutical products.

Other picolinic acid derivatives are also known from patent application EP-A-0 690 061 in which such compounds are used as synthesis intermediates for the preparation of pyridothiadiazoles.

Nevertheless, these known compounds have the disadvantage of being toxic products, this precluding any use of these compounds in agriculture for the eradication of phytopathogenic diseases of crops. Furthermore, these compounds are obtained from fermentation liquors and possess relatively complex chemical structures. Thus, the preparation and purification of these compounds remain delicate and expensive operations, making any industrial synthesis and marketing scarcely profitable.

We have now found a new family of picolinic acid derivative which do not possess the above mentioned drawbacks and which have an improved fungicidal activity.

Accordingly, the present invention relates to picolinic acid derivative of general formula (I):

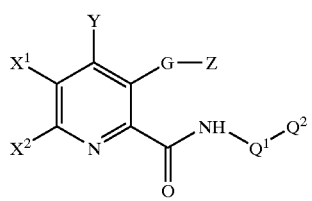

(I)

in which:

Y is chosen in the group consisting of $Y^1$ to $Y^3$:

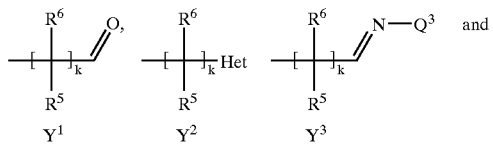

k represents 0, 1 or 2;

Het represents a five or six membered saturated or partially unsaturated or aromatic ring containing one to three heteroatoms of the group N, O, and S which can be identical or different and which can be substituted by one or two $-R^5$;

$Q^3$ is $-R^1$ or $-OR^1$;

G is chosen in the group consisting of $-(CH_2)_m-$, $-O-$, $-S-$ and $-NR^1$;

Z is chosen in the group consisting of $-R_1$, $C_1-C_4$ alkylene, $C_1-C_4$ alkylyne, $-Si(R^1)_3$, $-(CH_2)_p-$ OMe, $-(CH_2)_p-$SMe,

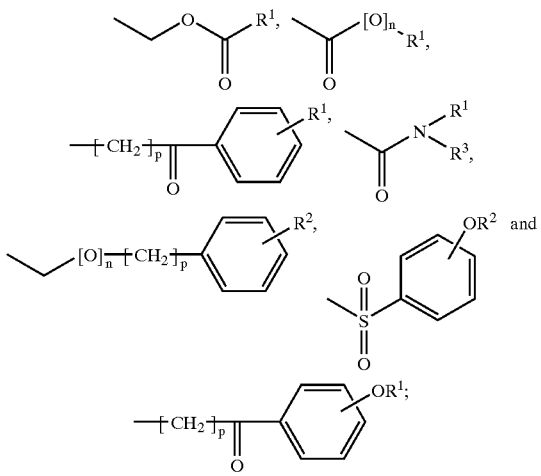

$X_1$ and $X_2$ are independently chosen in the group consisting of hydrogen, halogen, $-CF_3$, cyano group and nitro group;

$Q^1$ is chosen in the group consisting of $-(CH_2)_q-$,

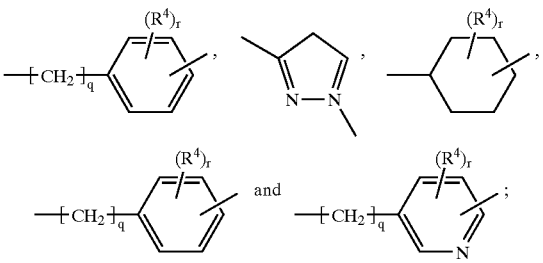

$Q^2$ is chosen in the group consisting of $-(O)_n-R^5$, cyano group,

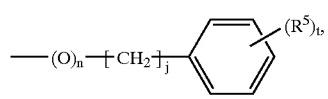

-continued

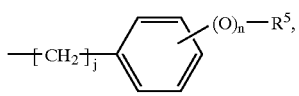

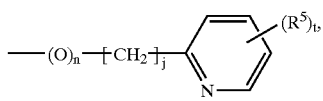

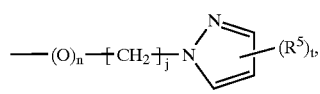

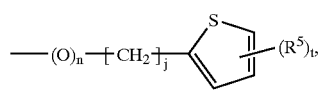

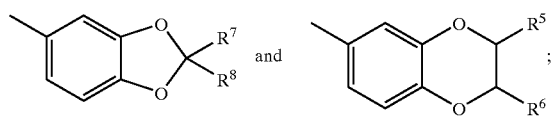

$R^1$ is hydrogen or $C_1$–$C_4$ alkyl;
$R^2$ is chosen in the group consisting of hydrogen, halogen, $C_1$–$C_4$ alkyl, $C_1$–$C_4$ alkoxy, $C_1$–$C_4$ halogenoalkyl and $C_1$–$C_4$ halogenoalkoxy;
$R^3$ is chosen in the group consisting of hydrogen, $C_1$–$C_4$ alkyl and $C_1$–$C_4$ alkoxyalkyl;
$R^4$ is chosen in the group consisting of halogen, $C_1$–$C_4$ alkyl and $C_1$–$C_4$ alkoxyalkyl;
$R^5$ and $R^6$ are independently of each other chosen in the group consisting of hydrogen, halogen, $C_1$–$C_4$ alkyl, $C_1$–$C_4$ halogenoalkyl;
$R^7$ and $R^8$ are independently of each other chosen in the group consisting of hydrogen and halogen;
n is 0 or 1;
j, m, p, q and t are independently chosen as being 0, 1, 2, 3 or 4;
r is 0, 1, 2 or 3;
and the optional N-oxides, geometric and/or optical isomers, enantiomers and/or diastereoisomers, tautomeric forms, salts, metal and metalloid complexes of the compounds of formula (I) as they have just been defined.

The tautomeric forms of the compound of general formula (I) are also included in the present invention. By tautomeric forms it is to be understood all of the isomeric forms well known in the art and as described in the work "The Tautomerism of Heterocycles, Advances in Heterocyclic Chemistry, Supplement 1, by J Elguero, C. Martin, A. R. Katritsky and P Linda, published by Academic Press, New York, 1976, pages 1–4.

The compound of general formula (I) can exist in one or more forms of geometrical isomers according to the number of double bonds in the compound. For example, compounds of general formula (I) can comprise 2 different geometrical isomers denoted (E) or (Z) depending on the configuration of the two double bonds. The E and Z notation can be replaced, respectively, by the term "syn" and "anti", or "cis" and "trans". Reference is made particularly to the work of E. Eliel and S. Wilen "Stereochemistry of Organic Compounds", published by Wiley (1994), for the description and use of these notations.

Preferably, the present invention relates to picolinic acid derivative of general formula (I) where the different substituents may be chosen independently from each other as being:

as regards Y of the general formula (I), Y is $Y^2$. More preferably, Y is chosen in the group consisting of pyrroles, dimethylpyrroles and imidazole.

as regards G of the general formula (I), G is O.

as regards $Q^1$ of the general formula (I), $Q^1$ is chosen in the group consisting of

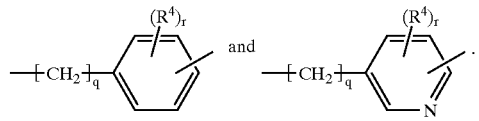

More preferably, the present invention relates to picolinic acid derivative of general formula (I) in which:

Y is $Y^2$,

G is O, and $Q^1$ is

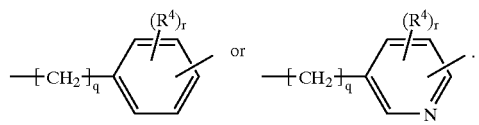

The compound of general formula (I) can exist in one or more optical isomeric or chiral forms according to the number of asymmetric centres in the compound. The present invention thus also includes all the optical isomers and their racemic or scalemic (scalemic designates a mixture of enantiomers in different proportions), as well as the mixtures of all possible stereoisomers in all proportions, including the racemic mixture. The separation of the diastereoisomers and/or optical isomers can be effected by known methods (E. Eliel ibid.).

The present invention also relates to a process of preparation of the compound of the general formula (I). Thus, according to a further aspect of the present invention there is provided a process for the preparation of compound of the general formula (I), characterised in that it comprises as a first step, the reaction scheme S-I:

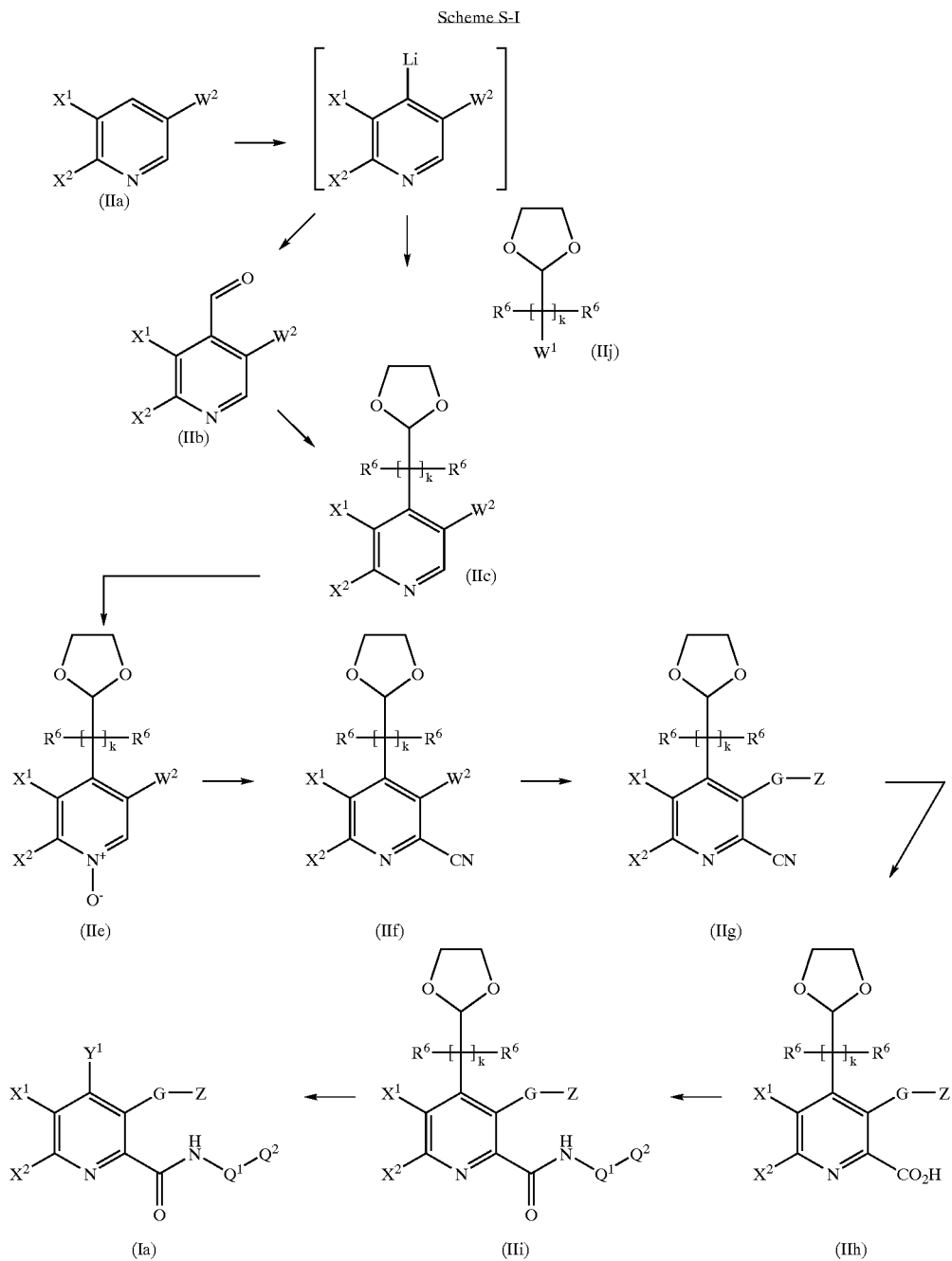

in which:

W$_1$ is chosen from bromine, chlorine and iodine;

W$_2$ is chosen from fluorine, chlorine, the group —O-DMG, the group —S-DMG and the group —NR$^1$—DMG; in which -DMG represents an ortho-directing metallation group such as those mentioned in the clarifications by V. Snieckus, *Chemical Reviews* (1990), pages 879–933, or by G. Quéguiner, *Tetrahedron* (2001), pages 4059–4090, k, R$^1$, R$^1$, R$^6$, X$^1$, X$^2$, Z, Q$^1$ and Q$^2$ are as defined above.

The ortho-lithiation of the pyridines of formula (IIa), according to methods such as those reported in the clarifications by V. Snieckus or G. Quéguiner cited above, makes it possible to prepare the compounds of formula (IIc), for which k represents 1 or 2, by reacting the intermediate lithium-containing pyridines with compounds of formula (IIj). The reaction of the same intermediates with formylation reagents such as dimethylformamide, ethyl formate, N-formylmorpholine or N-formylpiperidine, leads to the compounds of formula (IIb). The acetylation of the latter leads to the compounds of formula (IIc) for which k represents 0. The oxidation of the compounds of formula (IIc) with meta-chloroperbenzoic acid or hydrogen peroxide leads to the compounds of general formula (IIe). The latter are subjected to the Reissert-Henze reaction or, more advantageously, to the modification of this reaction described by W. K. Fife, *Journal of Organic Chemistry* (1983), pages 1375–1377, to give the compounds of formula (IIf). The cleavage of the DMG group or, when $W_2$ represents a fluorine or chlorine atom, aromatic nucleophilic substitution reactions make it possible to convert the compounds of formula (IIf) to compounds of formula (IIg). Hydrolysis with potassium or sodium hydroxide in aqueous medium of the cyano radical of the compounds of general formula (IIg) makes it possible to prepare the compounds of general formula (IIh). Conversion of the carboxyl radical of the compounds of general formula (IIh) according to methods well known to persons skilled in the art leads to the compounds of general formula (IIi) for which a reaction for hydrolysing the acetal group makes it possible to prepare the compounds of general formula (Ia).

as a second step, the preparation of the compound of general formula (Ic)

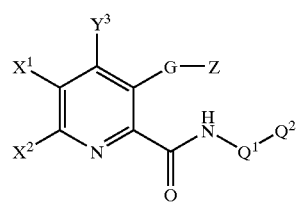

(Ic)

in which $Y^3$, $X^1$, $X^2$, G, Z, $Q^1$ and $Q^2$ are as defined above;

which compound may be prepared by reacting the compound of general formula (Ia) as defined above with a primary amine ($R_1$—$NH_2$), a hydrazine ($R^4R_5N$—$NH_2$) or a hydroxylamine ($R_2O$—$NH_2$), optionally in the presence of a Lewis acid and/or a water-capturing agent such as a molecular sieve.

The compound of general formula (Ib)

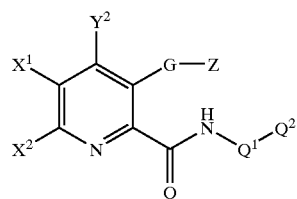

(Ib)

in which $Y^2$, $X^1$, $X^2$, G, Z, $Q^1$ and $Q^2$ are as defined above and the Het group is not directly linked to the rest of the structure (ie k=0) by a nitrogen atom may be prepared from the compounds of general formula (Ic) as defined above according to known heterocyclic methods of synthesis such as those reported in the book by A. R Katritzky "Handbook of heterocyclic chemistry", $2^{nd}$ edition, Ed. Pergamon (2000).

The compound of general formula (Ib) in which $Y^2$, $X^1$, $X^2$, G, Z, $Q^1$ and $Q^2$ are as defined above and the Het group is directly linked to the rest of the structure (ie k=0) by a nitrogen atom may be prepared from the compound of general formula (IIIa) (prepared according to methods described in WO 01/49667) according to scheme S-II:

Scheme S-II

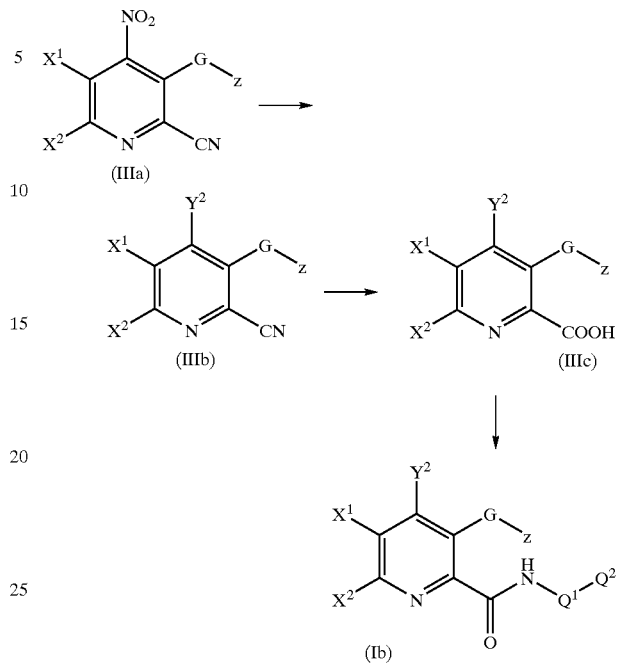

in which $Y^2$, $X^1$, $X^2$, G, Z, $Q^1$ and $Q^2$ are as defined above.

Aromatic nucleophilic substitution reactions with a base such as cesium or potassium carbonate in an aprotic solvent such as DMF or acetonitrile makes it possible to convert the compounds of formula (IIIa) to compounds of formula (IIIb). Hydrolysis with potassium or sodium hydroxide or with hydrochloric acid in aqueous medium of the cyano radical of the compounds of general formula (IIIb) makes it possible to prepare the compound of general formula (IIIc). Conversion of the carboxyl radical of the compound of general formula (IIIc) according to methods well known to persons skilled in the art leads to the compound of general formula (Ib).

The compound according to the present invention can be prepared according to the general method of preparation described above. It will nevertheless be understood that the skilled worker will be able to adapt this method according to the specifics of each of the compounds, which it is desired to synthesise.

The present invention also relates to fungicidal composition comprising an effective amount of an active material of general formula (I). Thus, according to the present invention, there is provided a fungicidal composition comprising, as an active ingredient, an effective amount of a compound as defined above and an agriculturally acceptable support.

In the present specification, the term "support" denotes a natural or synthetic, organic or inorganic material with which the active material is combined to make it easier to apply to the parts of the plant. This support is thus generally inert and should be agriculturally acceptable. The support may be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports may also be used.

The composition may also comprise additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active material and/or the inert support are water-insoluble and when the vector agent for the application is water. Preferably, surfactant content may be between 5% and 40% by weight.

Additional but optional components also include protective colloids, adhesives, thickeners, thixotropic agents, penetration agents, stabilisers, sequestering agents. More generally, the active materials can be combined with any solid or liquid additive, which complies with the usual formulation techniques.

In general, the composition according to the invention usually may contain from 0.05 to 99% (by weight) of active material.

Compositions according to the present invention can be used in quite diverse forms such as aerosol dispenser, bait(ready for use), bait concentrate, block bait, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, grain bait, granular bait, granule, hot fogging concentrate, macrogranule, microgranule, oil dispersible powder, oil miscible flowable concentrate, oil miscible liquid, paste, plant rodlet, plate bait, powder for dry seed treatment, scrap bait, seed coated with a pesticide, smoke candle, smoke cartridge, smoke generator, smoke pellet, smoke rodlet, smoke tablet, smoke tin, soluble concentrate, soluble powder, solution for seed treatment, suspension concentrate (flowable concentrate), tracking powder, ultra low volume (ulv) liquid, ultra low volume (ulv) suspension, vapour releasing product, water dispersible granules or tablets, water dispersible powder for slurry treatment, water soluble granules or tablets, water soluble powder for seed treatment and wettable powder.

These compositions include not only compositions which are ready to be applied to the plant or seed to be treated by means of a suitable device, such as a spraying or dusting device, but also concentrated commercial compositions which must be diluted before they are applied to the crop.

The compounds of the invention can also be mixed with one or more insecticides, fungicides, bactericides, attractant acaricides or pheromones or other compounds with biological activity. The mixtures thus obtained have a broadened spectrum of activity. In particular the compounds of the present invention do not exhibit the problem of cross-resistance with strobilurin derivatives. In fact the compounds of the present invention are active on a different biochemical site to strobilurin derivatives.

The mixtures with other fungicides are particularly advantageous, especially the mixtures with acibenzolar-S-methyl, benalaxyl, benomyl, blasticidin-S, bromuconazole, captafol, captan, carbendazim, carboxin, carpropamide, chlorothalonil, fungicidal compositions based on copper, derivatives of copper such as copper hydroxide and copper oxychloride, cyazofamide, cymoxanil, cyproconazole, cyprodinil, dichloran, diclocymet, diethofencarb, difenoconazole, diflumetorim, dimethomorph, diniconazole, dodemorph, dodine, edifenphos, epoxyconazole, ethaboxam, ethirimol, famoxadone, fenamidone, fenarimol, fenbuconazole, fenhexamide, fenpiclonil, fenpropidine, fenpropimorph, ferimzone, fluazinamn, fludioxonil, flumetover, fluquinconazole, flusilazole, flusulfamide, flutolanil, flutriafol, folpel, furalaxyl, furametpyr, guazatine, hexaconazole, hymexazol, imazalil, iprobenphos, iprodione, isoprothiolane, kasugamycin, mancozeb, maneb, mefenoxam, mepanipyrim, metalaxyl and their enantiomeric forms such as metalaxyl-M, metconazole, metiram-zinc, oxadixyl, pefurazoate, penconazole, pencycuron, phosphorous acid and its derivatives such as fosetyl-Al, phthalide, probenazole, prochloraz, procymidone, propamocarb, propiconazole, pyrimethanil, pyroquilon, quinoxyfen, silthiofam, simeconazole, spiroxamine, tebuconazole, tetraconazole, thiabendazole, thifluzamide, thiophanate, for example thiophanate-methyl, thiram, triadimefon, triadimenol, triazolopyrimidines e.g. cloransulam-methyl, flurnetsularn, florasulam, metosulam, tricyclazole, tridemorph, trifloxystrobin, triticonazole, derivatives of valinamide such as for example, iprovalicarb and benthiavalicarb, vinclozolin, zineb and zoxamide, as well as fungicide of the strobilurin familly, for example azoxystrobin, kresoxym-methyl, metominostrobin, discostrobin, dimoxystrobin, picoxystrobin, pyraclostrobin, and trifloxystrobin.

The fungicidal compositions of the present invention can be used to curatively or preventively combat the phytopathogenic fungi of crops. Thus, according to a further aspect of the present invention, there is provided a method for curatively or preventively combating the phytopathogenic fungi of crops characterised in that a fungicidal composition as hereinbefore defined is applied to the seed, the plant and/or to the fruit of the plant or to the soil in which the plant is growing or in which it is desired to grow.

The composition as used against phytopathogenic fungi of crops comprises an effective and non-phytotoxic amount of an active material of general formula (I).

The expression "effective and non-phytotoxic amount" means an amount of composition according to the invention which is sufficient to control or destroy the fungi present or liable to appear on the crops, and which does not entail any appreciable symptom of phytotoxicity for the said crops. Such an amount can vary within a wide range depending on the fungus to be combated, the type of crop, the climatic conditions and the compounds included in the fungicidal composition according to the invention.

This amount can be determined by systematic field trials, which are within the capabilities of a person skilled in the art.

The method of treatment according to the present invention is useful to treat propagation material such as tubers and rhizomes, but also seeds, seedlings or seedlings pricking out and plants or plants pricking out. This method of treatment can also be useful to treat roots. The method of treatment according to the present invention can also be useful to treat the overground parts of the plant such as trunks, stems or stalks, leaves, flowers and fruits of the concerned plant.

Among the plants targeted by the method according to the invention, mention may be made of cotton; flax; vine; fruit crops such as Rosaceae sp. (for instance pip fruits such as apples and pears, but also stone fruits such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantins), *Rubiaceae* sp., *Theaceae* sp., *Sterculiceae* sp., *Rutaceae* sp. (for instance lemons, oranges and grapefruits); leguminous crops such as *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); big crops such as *Graminde* sp. (for instance maize, cereals such as wheat, rice, barley and triticale), *Asteraceae* sp. (for instance sunflower), *Cruciferae* sp. (for instance colza), *Papilionaceae* sp. (for instance soja), *Solanaceae* sp. (for instance potatoes), *Chenopodiaceae* sp. (for instance beetroots); horticultural and forest crops; as well as genetically modified homologues of these crops.

Among the plants and the possible diseases of these plants targeted by the method according to the present invention, mention may be made of:

wheat, as regards controlling the following seed diseases: fusaria (*Microdochium nivale* and *Fusarium roseum*), stinking smut (*Tilletia caries, Tilletia controversa* or *Tilletia indica*), septoria disease (*Septoria nodorum*) and loose smut;

wheat, as regards controlling the following diseases of the aerial parts of the plant: cereal eyespot (*Tapesia yallundae, Tapesia acuiformis*), take-all (*Gaeumannomyces graminis*), foot blight (*F. culmorun, F. graminearum*), black speck (*Rhizoctonia cerealis*), powdery mildew (*Erysiphe graminis* formia specie *tritici*), rusts (*Puccinia striiformis* and *Puccinia recondita*) and septoria diseases (*Septoria tritici* and *Septoria nodorum*);

wheat and barley, as regards controlling bacterial and viral diseases, for example barley yellow mosaic;

barley, as regards controlling the following seed diseases: net blotch (*Pyrenophora graminea, Pyrenophora teres* and *Cochliobolus sativus*), loose smut (*Ustilago nuda*) and fusaria (*Microdochium nivale* and *Fusarium roseum*);

barley, as regards controlling the following diseases of the aerial parts of the plant: cereal eyespot (*Tapesia yallundae*), net blotch (*Pyrenophora teres* and *Cochliobolus sativus*), powdery mildew (*Erysiphe graminis* forma specie *hordei*), dwarf leaf rust (*Puccinia hordei*) and leaf blotch (*Rhynchosporium secalis*);

potato, as regards controlling tuber diseases (in particular *Helminthosporium solani, Phoma tuberosa, Rhizoctonia solani, Fusarium solani*), mildew (*Phytopthora infestans*) and certain viruses (virus Y);

potato, as regards controlling the following foliage diseases: early blight (*Alternaria solani*) mildew (*Phytophthora infestans*);

cotton, as regards controlling the following diseases of young plants grown from seeds: damping-off and collar rot (*Rhizoctonia solani, Fusarium oxysporum*) and black root rot (*Thielaviopsis basicola*);

protein yielding crops, for example peas, as regards controlling the following seed diseases: anthracnose (*Ascochyta pisi, Mycosphaerella pinodes*), fusaria (*Fusarium oxysporum*), grey mould (*Botrytis cinerea*) and mildew (*Peronospora pisi*);

oil-bearing crops, for example rape, as regards controlling the following seed diseases: *Phoma lingam, Alternaia brassicae* and *Sclerotinia sclerotiorum;* corn, as regards controlling seed diseases: (*Rhizopus* sp., *Penicillium* sp., *Trichoderma* sp., *Aspergillus* sp., and *Gibberella fujikuroi*);

flax, as regards controlling the seed disease: *Alternaria linicola;* forest trees, as regards controlling damping-off (*Fusarium oxysporum, Rhizoctonia solani*);

rice, as regards controlling the following diseases of the aerial parts: blast disease (*Magnaporthe grisea*), bordered sheath spot (*Rhizoctonia solani*);

leguminous crops, as regards controlling the following diseases of seeds or of young plants grown from seeds: damping-off and collar rot (*Fusarium oxysporum, Fusarium roseum, Rhizoctonia solani, Pythium* sp.);

leguminous crops, as regards controlling the following diseases of the aerial parts: grey mould (*Botrytis* sp.), powdery mildews (in particular *Erysiphe cichoracearum, Sphaerotheca fuliginea* and *Leveillula taurica*), fusaria (*Fusarium oxysporum, Fusarium roseum*), leaf spot (*Cladosporium* sp.), alternaria leaf spot (*Alternaria* sp.), anthracnose (*Colletotrichum* sp.), septoria leaf spot (*Septoria* sp.), black speck (*Rhizoctonia solani*), mildews (for example *Breimia lactucae, Peronospora* sp., *Pseudoperonospora* sp., *Phytophlthora* sp.);

fruit trees, as regards diseases of the aerial parts: monilia disease (*Monilia fructigenae, M. laxa*), scab (*Venturia inaequalis*), powdery mildew (*Podosphaera leucotricha*);

vine, as regards diseases of the foliage: in particular grey mould (*Botrytis cinerea*), powdery mildew (*Uncinula necator*), black rot (*Guignardia biwelli*) and mildew (*Plasmopara viticola*);

beetroot, as regards the following diseases of the aerial parts: cercospora blight (*Cercospora beticola*), powdery mildew (*Erysiphe beticola*), leaf spot (*Ramularia beticola*).

Cereals are preferably treated according to the method of the present invention. Wheat and rice are still preferred for carrying out the method according to the invention.

The fungicide composition according to the present invention may also be used against fungal diseases liable to grow on or inside lumber. The term "lumber" means all types of species of wood, and all types of working of this wood intended for construction, for example solid wood, high-density wood, laminated wood, and plywood. The method for treating lumber according to the invention consists in placing one or more compounds of the present invention, or a composition according to the invention, in contact. This placing in contact may cover the most diverse of forms such as, for example, direct application, spraying, dipping, injection or any other suitable means.

The dose of active material applied in the treatment according to the present invention is generally and advantageously between 10 and 800 g/ha, preferably between 50 and 300 g/ha for applications in foliar treatment. The dose of active material applied is generally and advantageously between 2 and 200 g per 100 kg of seed, preferably between 3 and 150 g per 100 kg of seed in the case of seed treatments. It is clearly understood that the doses indicated above are given as illustrative examples of the invention. A person skilled in the art will know how to tailor the application doses according to the nature of the crop to be treated.

The fungicidal composition according to the present invention may also be used in the treatment of genetically modified plants with the compounds according to the invention or the agrochemical compositions according to the invention. Genetically modified plants are plants into whose genome a heterologous gene encoding a protein of interest has been stably integrated. The expression "heterologous gene encoding a protein of interest" essentially means genes which give the transformed plant new agronomic properties, or genes for improving the agronomic quality of the transformed plant.

Among the genes which give the transformed plants new agronomic properties, mention may be made of genes which impart a tolerance to certain herbicides, those which impart a resistance to certain insects, those which impart a tolerance to certain diseases, etc. Such genes are described in particular in patent applications WO 91/02071 and WO 95/06128.

Among the genes which impart a tolerance to certain herbicides, mention may be made of the Bar gene imparting tolerance to bialophos, the gene encoding a suitable EPSPS imparting a resistance to herbicides having EPSPS as target, such as glyphosate and its salts (U.S. Pat. Nos. 4,535,060, 4,769,061, 5,094,945, 4,940,835, 5,188,642, 4,971,908, 5,145,783, 5,310,667, 5,312,910, 5,627,061, 5,633,435 and FR 2 736 926), the gene encoding glyphosate oxidoreductase (U.S. Pat. No. 5,463,175) or a gene encoding an HPPD imparting a tolerance to herbicides having HPPD as target, such as isoxazoles, in particular isoxafutol (FR 95/06800 and FR 95/13570), diketonitriles (EP-A-0 496 630 and EP-A-0 496 631) or triketones, in particular sulcotrioine (EP-A-0 625 505, EP-A-0 625 508 and U.S. Pat. No. 5,506,195). Such genes encoding an HPPD imparting a tolerance to herbicides having HPPD as target are disclosed in patent application WO 96/38567. In the case of genes encoding EPSPS or HPPD, and more particularly for the above genes, the sequence encoding these enzymes is advantageously preceded by a sequence encoding a transit peptide, in particular for the transit peptide known as optimized transit peptide, disclosed in patent U.S. Pat. No. 5,510,471.

Among the genes imparting novel insect-resistance properties, mention will be made more particularly of the genes encoding the Bt proteins which are widely described in the literature and well known to those skilled in the art. Mention will also be made of the genes encoding proteins extracted from bacteria such as *Photorabdus* (WO 97/17432 and WO 98/08932).

Among the genes imparting novel disease-resistance properties, mention will be made in particular of the genes encoding chitinases, glucanases and oxalate oxidase, all these proteins and their coding sequences being widely described in the literature, or genes encoding antibacterial and/or antifungal peptides, in particular cysteine-rich peptides containing less than 100 amino acids, such as plant thionines or defensines, and more particularly lytic peptides of all origins comprising one or more disulphide bridges between the cysteines and regions comprising basic amino acids, in particular the following lytic peptides: androctonine (WO 97/30082 and PCT/FR98/01814, filed on 18 Aug. 1998) or drosomicin (PCT/FR98/01462, filed on 8 Jul. 1998). Mention will also be made of the genes encoding fungal elicitor peptides, in particular the elicitins (Kamoun et al., 1993; Panabieres et al., 1995).

Among the genes which modify the constitution of modified plants, mention may be made in particular of genes which modify the content and quality of certain essential fatty acids (EP-A-0 666 918) or the content and quality of proteins, in particular in the leaves and/or seeds of the said plants. Mention will be made in particular of the genes encoding proteins that are rich in sulphur-containing amino acids (WO 98/20133; WO 97/41239; WO 95/31554; WO 94/20828 and WO 92/14822).

The fungicidal composition according to the present invention may, in particular, be used to the treatment of genetically modified plants comprising a heterologous gene, which gives the plant disease-resistance properties. The heterologous gene preferentially gives the genetically modified plant a spectrum of activity that is complementary to the spectrum of activity of the compounds according to the invention. According to the invention, the expression "complementary spectrum" means a spectrum of activity for the heterologous gene which is different from the spectrum of activity of the compounds according to the invention, or a spectrum of activity relating to identical infectious agents but allowing an identical or improved control for lower application doses of compounds according to the invention.

The compositions according to the present invention may also be used used to curatively or preventively treat human and animal fungal diseases such as, for example, mycoses, dermatoses, trichophyton diseases and candidiases or diseases caused by *Aspergillus* spp., for example *Aspergillus fumigatus*.

The aspects of the present invention will now be illustrated with reference to the following tables of compounds and examples. The following Tables I to III illustrate in a non-limiting manner examples of fungicidal compounds according to the present invention. In the following Examples, "MP" signifies "melting point" and is expressed in ° Celsius (° C.). M+1 (or M−1) means the molecular ion peak, plus or minus 1 a.m.u. (atomic mass units) respectively, as observed in mass spectroscopy.

TABLE I
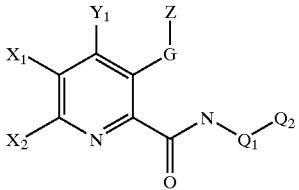

TABLE I-continued
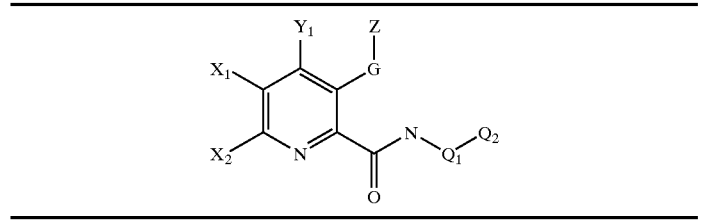
| | | | M + 1 = | |
|---|---|---|---|---|
| 1-2 | 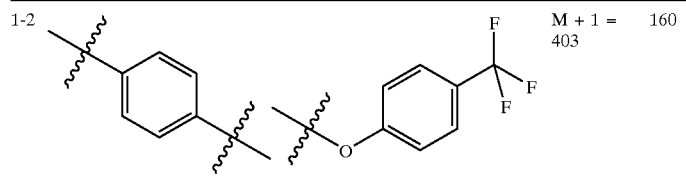 | | 403 | 160 |
| 1-3 | 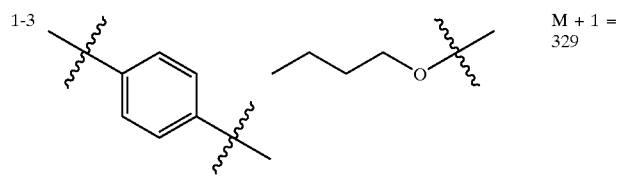 | | M + 1 = 329 | |
| 1-4 | 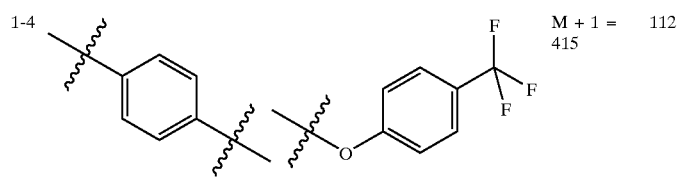 | | M + 1 = 415 | 112 |
| 1-5 | 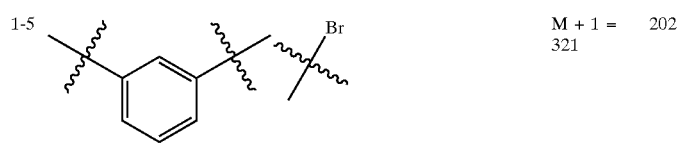 | | M + 1 = 321 | 202 |
| 1-6 | 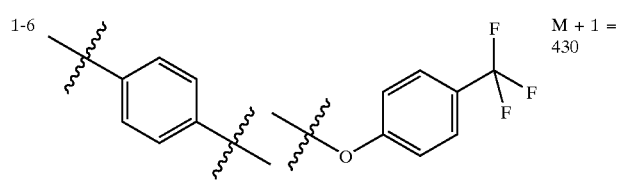 | | M + 1 = 430 | |

TABLE II

| N° | X1 | X2 | G | Z | Y | Q1 | Q2 | ion mol. | melting point |
|----|----|----|----|----|----|----|----|----|----|
| 2-1 | H | H | —S— | 4-methoxybenzyl | 4-methylpiperidin-1-yl | 1,4-phenylene | 4-methylphenoxy | M + 1 = 553 | |
| 2-2 | H | H | —S— | H | 4-methylpiperidin-1-yl | 1,4-phenylene | 4-methylphenoxy | M + 1 = 432 | |
| 2-3 | H | H | —S— | 4-methoxybenzyl | 3-methylpiperidin-1-yl | 1,4-phenylene | 4-methylphenoxy | M + 1 = 553 | |
| 2-4 | H | H | —S— | H | 3-methylpiperidin-1-yl | 1,4-phenylene | 4-methylphenoxy | M + 1 = 432 | |

TABLE II-continued

| N° | X1 | X2 | G | Z | Y | Q1 | Q2 | ion mol. | melting point |
|----|----|----|---|---|---|----|----|----------|---------------|
| 2-5 | H | H | O | H | pyrazolyl | p-phenylene | -OCF3 | | |
| 2-6 | H | H | O | H | pyrazolyl | p-phenylene | -O-(3-CF3-phenyl) | | |
| 2-7 | H | H | O | H | pyrazolyl | 3,3-dimethylcyclohexyl | | | |
| 2-8 | H | H | O | H | pyrazolyl | p-phenylene | -O-(4-CF3-phenyl) | | 131 |

TABLE II-continued

| N° | X1 | X2 | G | Z | Y | Q1 | Q2 | ion mol. | melting point |
|---|---|---|---|---|---|---|---|---|---|
| 2-9 | H | H | O | H | pyrazol-1-yl | 1,4-phenylene | benzyloxy | | |
| 2-10 | H | H | O | H | pyrazol-1-yl | 1,4-phenylene | butoxy | | |
| 2-11 | H | H | O | H | 4-methylimidazol-1-yl | 1,4-phenylene | 3-(trifluoromethyl)phenoxy | | |
| 2-12 | H | H | O | H | 4-methylimidazol-1-yl | 3,3,5-trimethylcyclohexyl | methyl | | |

TABLE II-continued

| N° | X1 | X2 | G | Z | Y | Q1 | Q2 | ion mol. | melting point |
|---|---|---|---|---|---|---|---|---|---|
| 2-13 | H | H | —O— | H | 4-methylimidazol-1-yl | 1,4-phenylene | 4-OCF3 | | |
| 2-14 | H | H | —O— | H | 4-methylimidazol-1-yl | 1,4-phenylene | 4-(4-trifluoromethylphenoxy) | | |
| 2-15 | H | H | —O— | H | 4-methylimidazol-1-yl | 1,4-phenylene | O-n-butyl | | 130 |

TABLE II-continued

| N° | X1 | X2 | G | Z | Y | Q1 | Q2 | ion mol. | melting point |
|---|---|---|---|---|---|---|---|---|---|
| 2-16 | H | H | –O– | H | 4-methylimidazol-1-yl | 1,4-phenylene | –O–CH2–C6H5 | | |
| 2-17 | H | H | –O– | H | 4-methylimidazol-1-yl | 1,3-phenylene | –O–CF3 | | |
| 2-18 | H | H | –O– | H | imidazol-1-yl | 1,4-phenylene | –O–CF3 | | |
| 2-19 | H | H | –O– | H | imidazol-1-yl | 1,4-phenylene | –O–CH2CH2CH2CH3 | | |

TABLE II-continued

| N° | X1 | X2 | G | Z | Y | Q1 | Q2 | ion mol. | melting point |
|---|---|---|---|---|---|---|---|---|---|
| 2-20 | H | H | O | H | imidazolyl | 1,4-phenylene | 3-(trifluoromethyl)phenoxy | | 155 |
| 2-21 | H | H | O | H | imidazolyl | 1,4-phenylene | benzyloxy | | |
| 2-22 | H | H | O | H | imidazolyl | 1,4-phenylene | 4-(trifluoromethyl)phenoxy | | |
| 2-23 | H | H | O | H | imidazolyl | 3,3,5-trimethylcyclohexyl | | | |

TABLE II-continued

| N° | X1 | X2 | G | Z | Y | Q1 | Q2 | ion mol. | melting point |
|---|---|---|---|---|---|---|---|---|---|
| 2-24 | H | H | O | H | imidazolyl | 1,3-phenylene | C(CF₃)F₂ | | |
| 2-25 | H | H | O | H | imidazolyl | (methyl branch) | 2,2-difluoro-benzo[1,3]dioxole | | |
| 2-26 | H | H | O | H | imidazolyl | pyridine-2,6-diyl-ethyl | H | | |
| 2-27 | H | H | O | H | imidazolyl | 1,4-phenylene | CN | | |

TABLE II-continued

| N° | X1 | X2 | G | Z | Y | Q1 | Q2 | ion mol. | melting point |
|---|---|---|---|---|---|---|---|---|---|
| 2-28 | H | H | O- | H | imidazol-1-yl | 1,4-phenylene | 5-(trifluoromethyl)pyrazol-1-yl | | |
| 2-29 | H | H | O- | H | imidazol-1-yl | 1,4-phenylene | n-butyloxy | | |
| 2-30 | H | H | O- | H | imidazol-1-yl | 1,4-phenylene | 3-(trifluoromethyl)phenoxy | | |
| 2-31 | H | H | O- | H | imidazol-1-yl | 1,4-phenylene | trifluoromethoxy | | |

TABLE II-continued

| N° | X1 | X2 | G | Z | Y | Q1 | Q2 | ion mol. | melting point |
|---|---|---|---|---|---|---|---|---|---|
| 2-32 | H | H | O | H | imidazolyl | 1,4-phenylene | 4-(trifluoromethyl)phenoxy | | 172 |
| 2-33 | H | H | O | H | imidazolyl | 1,4-phenylene | benzyloxy | | |
| 2-34 | H | H | O | H | imidazolyl | 4,4-dimethylcyclohexyl | methyl | | |
| 2-35 | H | H | O | H | imidazolyl | 1,3-phenylene | trifluoromethyl | | |

TABLE II-continued

| N° | X1 | X2 | G | Z | Y | Q1 | Q2 | ion mol. | melting point |
|---|---|---|---|---|---|---|---|---|---|
| 2-36 | H | H | O | H | imidazole | — | 2,2-difluoro-benzodioxole | | |
| 2-37 | H | H | O | H | imidazole | phenyl | CN | | |
| 2-38 | H | H | O | H | imidazole | pyridine | H | | |
| 2-39 | H | H | O | H | pyrazole | phenyl | OBu | | |

TABLE II-continued

| N° | X1 | X2 | G | Z | Y | Q1 | Q2 | ion mol. | melting point |
|---|---|---|---|---|---|---|---|---|---|
| 2-40 | H | H | O | H | pyrazolyl | phenyl | OCF₃ | | |
| 2-41 | H | H | O | H | pyrazolyl | phenyl | O-C₆H₄-CF₃ (para) | | 113 |
| 2-42 | H | H | O | H | pyrazolyl | phenyl | O-C₆H₄-CF₃ (meta) | | |
| 2-43 | H | H | O | H | pyrazolyl | trimethylcyclohexyl | | | |

TABLE II-continued

| N° | X1 | X2 | G | Z | Y | Q1 | Q2 | ion mol. | melting point |
|---|---|---|---|---|---|---|---|---|---|
| 2-44 | H | H | O | H | pyrazol-1-yl | 1,4-phenylene | OCH2-phenyl | | |
| 2-45 | H | H | O | H | 3-methylpyrazol-1-yl | 1,4-phenylene | O-(3-trifluoromethylphenyl) | | |
| 2-46 | H | H | O | H | 3-methylpyrazol-1-yl | 1,4-phenylene | OCF3 | | |
| 2-47 | H | H | O | H | 3-methylpyrazol-1-yl | 3,3,5-trimethylcyclohexyl | | | |

TABLE II-continued

| N° | X1 | X2 | G | Z | Y | Q1 | Q2 | ion mol. | melting point |
|---|---|---|---|---|---|---|---|---|---|
| 2-48 | H | H | —O— | H | 4-methylpyrazol-1-yl | 1,4-phenylene | 4-(trifluoromethyl)phenoxy | | 138 |
| 2-49 | H | H | —O— | H | 4-methylpyrazol-1-yl | 1,4-phenylene | n-butoxy | | |
| 2-50 | H | H | —O— | H | 4-methylpyrazol-1-yl | 1,4-phenylene | benzyloxy | | |

TABLE II-continued

| N° | X1 | X2 | G | Z | Y | Q1 | Q2 | ion mol. | melting point |
|---|---|---|---|---|---|---|---|---|---|
| 2-51 | H | H | O | H | 4-methylpyrazol-1-yl | 1,3-phenylene | OCF₃ | | |
| 2-52 | H | H | O | H | 4-methylpyrazol-1-yl | 3-chloro-pyridinyl-CH₂ | C(CH₃)(CF₃) | | |
| 2-53 | H | H | O | H | 4-methylpyrazol-1-yl | pyridin-2,5-diyl | O-(4-fluorophenyl) | | |

TABLE II-continued

| N° | X1 | X2 | G | Z | Y | Q1 | Q2 | ion mol. | melting point |
|---|---|---|---|---|---|---|---|---|---|
| 2-54 | H | H | —O— | H | 3-methylpyrazol-1-yl | 1,4-phenylene | —OCF$_3$ | | |
| 2-55 | H | H | —O— | H | 3-methylpyrazol-1-yl | 3,3,5-trimethylcyclohexyl | —CH$_3$ | | |
| 2-56 | H | H | —O— | H | 3-methylpyrazol-1-yl | 1,4-phenylene | 3-(trifluoromethyl)phenoxy | | |

TABLE II-continued

| N° | X1 | X2 | G | Z | Y | Q1 | Q2 | ion mol. | melting point |
|---|---|---|---|---|---|---|---|---|---|
| 2-57 | H | H | —O— | H | 3-methyl-pyrazol-1-yl | 1,4-phenylene | benzyloxy | | 159 |
| 2-58 | H | H | —O— | H | 3-methyl-pyrazol-1-yl | 1,4-phenylene | 4-(trifluoromethyl)phenoxy | | |
| 2-59 | H | H | —O— | H | 3-(trifluoromethyl)-pyrazol-1-yl | 1,4-phenylene | 3-(trifluoromethyl)phenoxy | | |

TABLE II-continued

| N° | X1 | X2 | G | Z | Y | Q1 | Q2 | ion mol. | melting point |
|---|---|---|---|---|---|---|---|---|---|
| 2-60 | H | H | O | H | 3-(trifluoromethyl)pyrazol-1-yl | 3,3,5-trimethylcyclohexyl | (unsubstituted) | | |
| 2-61 | H | H | O | H | 3-(trifluoromethyl)pyrazol-1-yl | 1,4-phenylene | OCF3 | | |
| 2-62 | H | H | O | H | 3-(trifluoromethyl)pyrazol-1-yl | 1,4-phenylene | O-(4-trifluoromethylphenyl) | | |

TABLE II-continued

| N° | X1 | X2 | G | Z | Y | Q1 | Q2 | ion mol. | melting point |
|---|---|---|---|---|---|---|---|---|---|
| 2-63 | H | H | —O— | H | 3-(CF$_3$)-pyrazol-1-yl | 1,4-phenylene | n-butoxy | | |
| 2-64 | H | H | —O— | H | 3-(CF$_3$)-pyrazol-1-yl | 1,4-phenylene | benzyloxy | | |
| 2-65 | H | H | —O— | H | 3-(CF$_3$)-pyrazol-1-yl | 1,3-phenylene | C(CF$_3$)$_2$F | | 118 |

TABLE II-continued

| N° | X1 | X2 | G | Z | Y | Q1 | Q2 | ion mol. | melting point |
|---|---|---|---|---|---|---|---|---|---|
| 2-66 | H | H | —O— | H | 3-(trifluoromethyl)pyrazol-1-yl | CH | 2,2-difluoro-1,3-benzodioxol-5-yl | | |
| 2-67 | H | H | —O— | H | 3-(trifluoromethyl)pyrazol-1-yl | CH₂CH₂ | pyridin-2,6-diyl-H | | |
| 2-68 | H | H | —O— | H | 2,6-dimethylmorpholin-4-yl | CH | 4-(trifluoromethoxy)phenyl / phenyl | | 160 |

TABLE II-continued

| N° | X1 | X2 | G | Z | Y | Q1 | Q2 | ion mol. | melting point |
|---|---|---|---|---|---|---|---|---|---|
| 2-69 | H | H | O | H | piperazine | 1,4-phenylene | -OCH₂CH₂CH₃ | | |
| 2-70 | H | H | O | H | piperazine | 1,4-phenylene | 3-(trifluoromethyl)phenoxy | | |
| 2-71 | H | H | O | H | pyrrolidine | 1,4-phenylene | -OCH₂CH₂CH₃ | | |

TABLE II-continued

| N° | X1 | X2 | G | Z | Y | Q1 | Q2 | ion mol. | melting point |
|---|---|---|---|---|---|---|---|---|---|
| 2-72 | H | H | —O— | H | pyrrolidine | phenyl | 3-CF₃-phenoxy | | 156 |
| 2-73 | H | H | —S— | 4-methoxybenzyl | pyrrolidine | phenyl | 3-CF₃-phenoxy | M+1 = 580 | |
| 2-74 | H | H | —O— | H | thiomorpholine | phenyl | butoxy | | 140 |
| 2-75 | H | H | —O— | H | thiomorpholine | phenyl | 4-CF₃-phenoxy | | |

TABLE II-continued

| N° | X1 | X2 | G | Z | Y | Q1 | Q2 | ion mol. | melting point |
|---|---|---|---|---|---|---|---|---|---|
| 2-76 | H | H | —O— | H | thiomorpholinyl | 1,4-phenylene | 3-(trifluoromethyl)phenoxy | | |
| 2-77 | H | H | —S— | CH2-(4-methoxyphenyl) | thiomorpholinyl | 1,4-phenylene | 4-methylphenoxy | M+1 = 557 | |
| 2-78 | H | H | —O— | H | morpholinyl | 1,4-phenylene | butoxy | | |
| 2-79 | H | H | —O— | H | morpholinyl | 1,4-phenylene | 3-(trifluoromethyl)phenoxy | | |

TABLE II-continued

| N° | X1 | X2 | G | Z | Y | Q1 | Q2 | ion mol. | melting point |
|---|---|---|---|---|---|---|---|---|---|
| 2-80 | H | H | —O— | H | morpholine | 1,4-phenylene | 4-(trifluoromethyl)phenoxy | | 143 |
| 2-81 | H | H | —O— | isopropyl | piperidine | 1,4-phenylene | 4-methylphenoxy | | |
| 2-82 | H | H | —O— | H | piperidine | 1,4-phenylene | 4-methylphenoxy | | |
| 2-83 | H | H | —O— | H | piperidine | 1,4-phenylene | n-butoxy | | |

TABLE II-continued

| N° | X1 | X2 | G | Z | Y | Q1 | Q2 | ion mol. | melting point |
|---|---|---|---|---|---|---|---|---|---|
| 2-84 | H | H | O | H | piperidine | 1,4-phenylene | 4-(trifluoromethyl)phenoxy | | |
| 2-85 | H | H | O | H | piperidine | 1,4-phenylene | 3-(trifluoromethyl)phenoxy | | |
| 2-86 | H | H | O | methyl | piperidine | 1,4-phenylene | 4-methylphenoxy | | |
| 2-87 | H | H | S | methyl | piperidine | 1,4-phenylene | benzyloxy | | |

TABLE II-continued

| N° | X1 | X2 | G | Z | Y | Q1 | Q2 | ion mol. | melting point |
|---|---|---|---|---|---|---|---|---|---|
| 2-88 | H | H | —S— | 4-methoxybenzyl | piperidin-1-yl | 1,4-phenylene | 3-(trifluoromethyl)phenoxy | M+1 = 592 | |
| 2-89 | H | H | —S— | H | piperidin-1-yl | 1,4-phenylene | 3-(trifluoromethyl)phenoxy | | |
| 2-90 | H | H | —S— | 4-methoxybenzyl | piperidin-1-yl | 1,4-phenylene | 4-methylphenoxy | | |
| 2-91 | H | H | —O— | H | pyrrol-1-yl | 1,4-phenylene | 4-(trifluoromethyl)phenoxy | M+1 = 440 | 159 |

TABLE II-continued

| N° | X1 | X2 | G | Z | Y | Q1 | Q2 | ion mol. | melting point |
|---|---|---|---|---|---|---|---|---|---|
| 2-92 | H | H | —O— | H | pyrrol-1-yl | p-phenylene | butoxy | M+1 = 452 | |
| 2-93 | H | H | —O— | H | pyrrol-1-yl | p-phenylene | 3-(trifluoromethyl)phenoxy | M+1 = 438 | |
| 2-94 | H | H | —O— | H | 2,5-dimethylpyrrol-1-yl | p-phenylene | 4-(trifluoromethyl)phenoxy | M+1 = 468 | |
| 2-95 | H | H | —O— | H | 2,5-dimethylpyrrol-1-yl | p-phenylene | phenoxy | M+1 = 400 | |

TABLE II-continued

| N° | X1 | X2 | G | Z | Y | Q1 | Q2 | ion mol. | melting point |
|---|---|---|---|---|---|---|---|---|---|
| 2-96 | H | H | —O— | H | 2,5-dimethylpyrrol-N-yl | 1,4-phenylene | 3-(trifluoromethyl)phenoxy | M+1 = 468 | |
| 2-97 | H | H | —O— | H | 1,3-dioxolan-2-yl | 1,4-phenylene | 4-(trifluoromethyl)phenoxy | M+1 = 461 | 76 |
| 2-98 | H | H | —O— | H | 1,3-dioxolan-2-yl | 1,4-phenylene | butoxy | M+1 = 373 | |
| 2-99 | H | H | —O— | H | 1,3-dioxolan-2-yl | 1,4-phenylene | 4-(trifluoromethyl)phenoxy | M+1 = 447 | |

TABLE II-continued

| N° | X1 | X2 | G | Z | Y | Q1 | Q2 | ion mol. | melting point |
|---|---|---|---|---|---|---|---|---|---|
| 2-100 | H | H | —O— | | pyrrol-1-yl | 1,4-phenylene | 4-(trifluoromethyl)phenoxy | M+1 = 454 | |
| 2-101 | H | H | —O— | | pyrrol-1-yl | 1,4-phenylene | 3-(trifluoromethyl)phenoxy | M+1 = 454 | |
| 2-102 | H | H | —O— | | pyrrol-1-yl | bond | 3-bromophenyl | M+1 = 372 | |
| 2-103 | H | H | —O— | | 2,5-dimethylpyrrol-1-yl | 1,4-phenylene | 4-(trifluoromethyl)phenoxy | M+1 = 482 | |

TABLE II-continued

| N° | X1 | X2 | G | Z | Y | Q1 | Q2 | ion mol. | melting point |
|---|---|---|---|---|---|---|---|---|---|
| 2-104 | H | H | —O— | (tBu) | 2,5-dimethylpyrrol-1-yl | 1,4-phenylene | 3-(trifluoromethyl)phenoxy | M + 1 = 482 | |

TABLE III

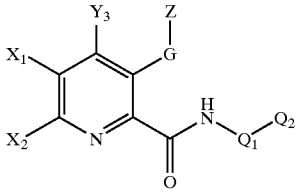

| N° | X1 | X2 | G | Z | Y |
|---|---|---|---|---|---|
| 3-1 | —H | —H | —O— | —H | =N—OH |
| 3-2 | —H | —H | —O— | —H | =N—OH |

| N° | Q1 | Q2 | ion mol. | melting point |
|---|---|---|---|---|
| 3-1 | (1,3-phenylene) | —Br | M + 1 = 336 | |
| 3-2 | (1,4-phenylene) | —O—(4-CF$_3$-phenyl) | M + 1 = 418 | |

EXAMPLES OF PROCESS FOR PREPARATION OF THE COMPOUNDS OF GENERAL FORMULA (I)

EXAMPLE

Preparation of Picolinic Acid Derivatives of Formula (I)
3-fluoro-4-(1,3-dioxolan-2-yl)pyridine-N-oxyde (example of compound of formula IIe according to scheme S-1)

11.1 g (80 mmol) of 3-fluoro-4-formyl-pyridine (prepared according to the methods described in Queginner, Tetrahedron, (1983), pages 2021) are dissolved in 50 ml of toluene. 6.2 ml (112 mmol) of anhydride ethylene glycol, 17.0 g (88 mmol) of paratoluene sulfonic acid and 250 ml of toluene are added successively. The resulting solution is heated at 130° C. whilst the water formed is removed with a dean-stark. When the reaction is finished, the mixture is cooled down and the toluene removed in vacuum. The residue is taken up in a mixture of 200 ml of chloroform and 100 ml of a 1M sodium hydroxide solution. The phases are separated, and the aqueous phase is further extracted with chloroform. The organic phases are washed with brine, dried and solvent evaporated. The residue is taken up in 100 ml of dichloromethane, and a solution of 22.0 g (88 mmol) meta-chloro-perbenzoyc acid in 200 ml of dichloromethane is added. The resulting solution is stirred at room temperature overnight. 22 g of potassium carbonate in 22 ml of water were added, and the resulting mixture is stirred for 20 minutes, before being filtered off on celite. The filtrate was dried and solvent evaporated to give 11.8 g (79% yield) of a yellow oil (M+1=186).

2-cyano-3-fluoro-4-(1,3-dioxolan-2-yl)pyridine (example of compound of formula IIf according to scheme S-1)

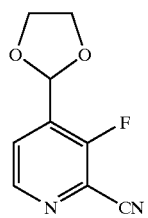

4 g (21,6 mmol) of 3-fluoro-4-(1,3-dioxolan-2-yl)-pyridine-N-oxyde are dissolved in 34 ml of acetonitrile. 9.1 ml (64.8 mmol) of triethylamine, followed by 8.6 ml (64.8 mmol) of trimethylsilyl cyanide are added and the resulting solution is heated at reflux for 12 hours. The solvent is evaporated and the residue is taken up in a mixture of 70 ml of ethyl acetate, 70 ml of water and 34 g of potassium carbonate. The organic phases are washed with brine, dried filtrated on celite and solvent evaporated. Purification on silica give 3.7 g (88% yield) of a brown oil (M+1=195) 3-fluoro-4-(1,3-dioxolan-2-yl)picolinic acid

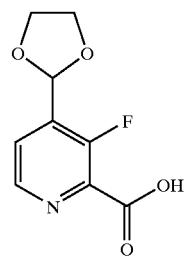

A mixture of 4.1 g (21 mmol) of 2-cyano-3-fluoro-4-(1,3-dioxolan-2-yl)-pyridine, 2.1 g (53 mmol) sodium hydroxide in 100 ml of water is heated at 90° C. for 2 hours. After cooling, the reaction mixture is acidified to pH=1 with aqueous hydrochloric acid, then extracted with ethyl acetate. The organic phases are washed with brine, dried filtrated on celite and solvent evaporated. There is obtained 2.4 g (53% yield) of a white solid (M+1=214)
2-{N-para-[4-(trifluoromethylphenoxy)phenyl]}aminocarbonyl-3-fluoro-4-(1,3-dioxolan-2-yl)pyridine

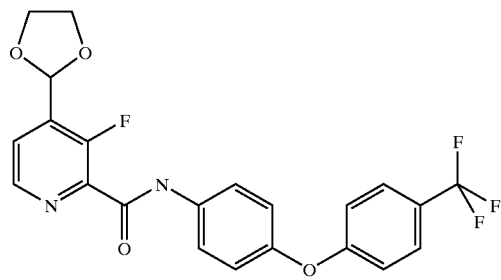

To a mixture of 0.95 g (4.5 mmol) 3-fluoro-4-(1.3-dioxolan-2-yl) picolinic acid and 1.1 g (4.5 mmol) of para-[4-(trifluoromethylphenoxy)]aniline in 30 ml of dichloromethane are added 0.95 g (4.5 mmol) of 1-(3-dimethylaminopropyl)-3-ehtyl carbodiimide chlorhydrate. The mixture is stirred at room temperature for 3 hours. After solvent evaporation, the residue is purified on silica. There is obtained 1.6 g (80% yield) of a cream solid (M+1=449) 2-{N-para-[4-(trifluoromethylphenoxy)phenyl]}aminocarbonyl-3-hydroxy-4-(1,3-dioxolan-2-yl)pyridine (compounds n° 2–99)

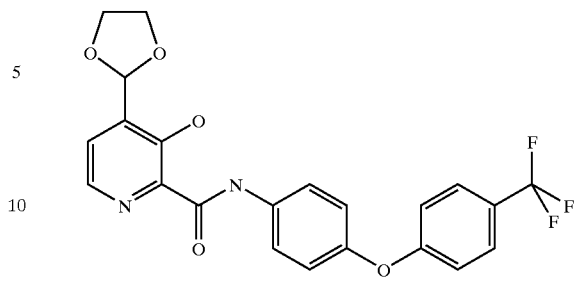

A mixture of 200 mg (0.45 mmol) of 2-{N-para-[4-(trifluoromethylphenoxy)phenyl]} aminocarbonyl-3-fluoro-4-(1,3-dioxolan-2-yl)pyridine, few drops of water, 4 ml of DMSO and 125 mg (2.2 mmol) of potassium hydroxide is heated at 100° C. for 16 hours. After cooling, the reaction mixture is acidified with a 1 M aqueous hydrochloric acid solution, and extracted with ethyl acetate. The organic phases are washed with brine, dried and solvent evaporated. There is obtained 139 mg (69% yield) of a brown oil (M+1=447)
2-{N-para-[4-(trifluoromethylphenoxy)phenyl]}aminocarbonyl-3-hydroxy-4-formyl pyridine (compounds no 1–2)

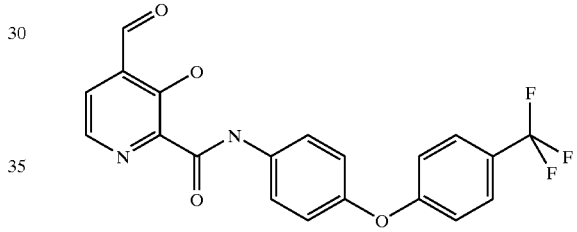

A solution of 131 mg (0.29 mmol) of 2-{N-para-[4-(trifluoromethylphenoxy)phenyl]}aminocarbonyl-3-hydroxy-4-(1,3-dioxolan-2-yl)pyridine in 1 ml of formic acid and 1 ml of water is heated at 100° C. for 3 hours. After cooling, the resulting precipitate is filtered off, rinced with water, triturated with a mixture of diisopropyl ether and heptane, filtered off and dried. There is obtained 67 mg (57% yield) of a cream solid (M+1=403)
2-{N-(3-bromophenyl)aminocarbonyl}-3-hydroxy-4-carboxaldehyde oxime pyridine (compounds 3–1)

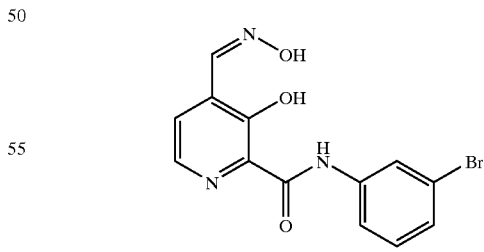

A mixture of 50 mg (0.160 mmol) of 2-{N-(3-bromophenyl) aminocarbonyl}-3-hydroxy-4-formyl pyridine, 11,4 mg (0.164 mmol) of hydroxylamine hydrate, 32 mg of Amberlyst A-21 and 1 ml of ethanol is stirred at room temperature overnight. The resin is filtered off and rinsed with dichloromethane The filtrate is evaporated to give 54 mg (100% yield) of a brown solid.(M+1=336)

2-{N-para-[4-(trifluoromethylphenoxy)phenyl]}aminocarbonyl-3-hydroxy-4-(2,5 dimetyl pyrrol-1-yl) pyridine (compounds 2–94)

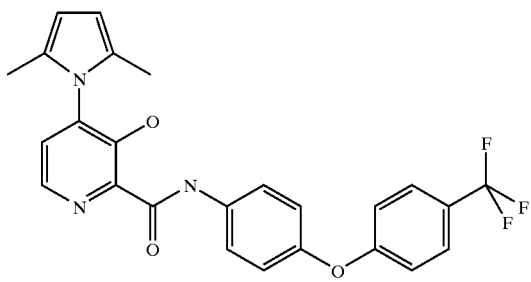

A mixture of 0.5 g (1.29 mmol) 2-{N-para-[4-(trifluoromethylphenoxy)phenyl]}aminocarbonyl-3-hydroxy-4-amino pyridine (prepared according to the method described in WO 0149666) and 293 mg acetonylacetone (2.57 mmol) in 5 ml of glacial acetic acid, is refluxed for 24 hours over a dean and stark containing 4A molecular sieves. The reaction is cooled and solvent evaporated, the residue is dissolved in dichloromethane and washed with aqueous sodium bicarbonate, the organic phase was dried over MgSO4 and solvent evaporated. The crude product was chromatographed on silica to yield 157 mg (26% yield) of a brown oil. (M+1=468)

2-{N-meta-[4-(trifluoromethylphenoxy)phenyl]}aminocarbonyl-3-hydroxy-4-(pyrrol-1-yl)pyridine (compounds 2–93)

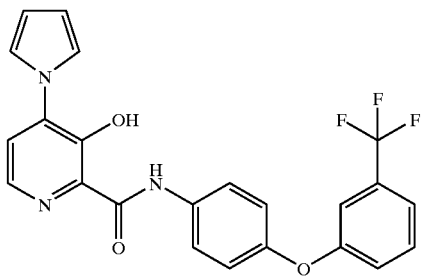

A mixture of 0.2 g (0.51 mmol) 2-{N-meta-[4-(trifluoromethylphenoxy)phenyl]} aminocarbonyl-3-hydroxy-4-amino pyridine (prepared according to the method described in WO 0149666) and 78 mg (0.56 mmol) of 2,5-dimethoxytetrahydrofuran) in 1 ml of glacial acetic acid, is heated at 110° C. for 1 hour. The reaction is cooled and solvent evaporated, the residue is dissolved in dichloromethane and washed with aqueous sodium bicarbonate, the organic phase was dried over MgSO$_4$ and solvent evaporated. The crude product was chromatographed on silica to yield 137 mg (61% yield) of a yellow solid. (M+1=440)

2-N-(3-trifluoromethyl phenyl) aminocarbonyl-3-hydroxy-4-(imidazol-1-yl) pyridine (compound 2–24)

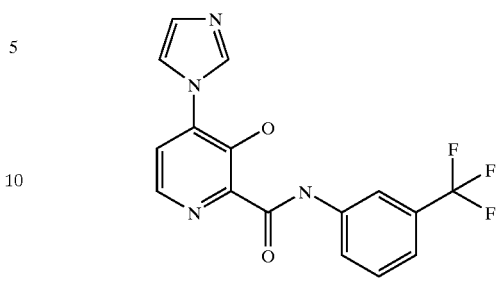

A mixture of 1.36 g (20 mmol) of imidazol and 60.52 g (20 mmol) of cesium carbonate is stirred at room temperature in 20 ml of DMF for 20 minutes. 3.58 g (20 mmol) of 4-nitro-3-methoxy-2-cyano pyridine (prepared according to the methods described in WO 0149667) is added in one pot and the mixture is stirred overnight. DMF is removed in vacuo and the residue is partitioned between water and ethyl acetate. The aqueous phase is further extracted with ethyl acetate. The organic phases are washed with dilute brine, dried and solvent evaporated. Purification on silica gave 1.4 g of 4-(imidazol-1-yl)-3-methoxy-2-cyano pyridine.

A mixture of 1.4 g (7 mmol) of 4-(imidazol-1-yl)-3methoxy-2-cyano pyridine in 12 mls of concentrated hydrochloric acid is heated at 85° C. overnight. After cooling, the solvent is evaporated to dryness, more water is added and the solvent is evaporated. This is done 4 times, little water is added to the residue and the precipitate is filtered off and dried in an oven at 60° C. over P$_2$O$_5$ under vacuum for 2 hours. There is obtained 0.8 g of 4-(imidazol-1-yl)-3-methoxy nicotinic acid.

To a stirred mixture of 144 mg (0.7 mmol) of 4-(imidazol-1-yl)-3-methoxy nicotinic acid, 95 mg (0.95 mmol) of HOBT and 113 mg (0.7 mmol) of 3-trifluoromethyl aniline in 5 ml of pyridine is added 134 mg (0.87 mmol) of EDCI. The mixture is stirred at reflux for 1.5 hours and at room temperature overnight. The solvent was evaporated and the residue is partitioned between water and dichloromethane. The aqueous phase is further extracted with dichloromethane. The organic phases are washed with dilute brine, dried and solvent evaporated. Purification on silica yielded 97 mg (40% yield) of a yellow solid (M+1=349).

EXAMPLES OF BIOLOGICAL ACTIVITY OF THE COMPOUNDS OF THE INVENTION

Example A

In Vivo Test on *Alternaria brassicae* (Leaf Spot of Crucifers)

An aqueous suspension, at a concentration of 1.5%, of the active material tested is obtained by grinding it finely in a formulation of concentrated suspension type. This aqueous suspension is then diluted in water so as to obtain the desired active material concentration. Radish plants (Pernot variety) in starter cups, sown on a 50/50 peat soil-pozzolana substrate and grown at 18–20° C., are treated at the cotyledon stage by spraying with the aqueous suspension described above. Plants, used as controls, are treated with an aqueous solution not containing the active material.

After 24 hours, the plants are contaminated by spraying them with an aqueous suspension of *Alternaria brassicae* spores (40,000 spores per cm$^3$). The spores are collected from a 12–13 day-old culture. The contaminated radish plants are incubated for 6–7 days at about 18° C., under a humid atmosphere. Grading is carried out 6 to 7 days after the contamination, in comparison with the control plants. Under these conditions, good (at least 50%) or total protection is observed at a dose of 500 g/ha with the following compounds: 1-1, 1-2, 2-10, 2-11, 2-12, 2-13, 2-14, 2-15, 2-16, 2-17, 2-18, 2-19, 2-20, 2-21, 2-22, 2-23, 2-24, 2-25, 2-29, 2-30, 2-31, 2-32, 2-34, 2-35, 2-362, 2-38, 2-42, 2-522-47, 2-48, 2-49, 2-51, 2-52, 2-53, 2-56, 2-59, 2-60, 2-61, 2-67, 2-83, 2-85, 2-93, 2-94,2-96, 2-97.

Example B

In Vivo Test on *Septoria nodorum* (Wheat Glume Blotch)

An aqueous suspension, at a concentration of 1.5%, of the active material tested is obtained by grinding it finely in a formulation of concentrated suspension type. This aqueous suspension is then diluted in water so as to obtain the desired active material concentration.

Wheat plants (Scipion variety) in starter cups, sown on a 50/50 peat soil-pozzolana substrate and grown at 12° C., are treated at the 1-leaf stage (10 cm tall) by spraying them with the aqueous suspension described above. Plants, used as controls, are treated with an aqueous solution not containing the active material. After 24 hours, the plants are contaminated by spraying with an aqueous suspension of *Septoria nodorum* spores (500,000 spores per cm$^3$). The spores are collected from a seven-day-old culture. The contaminated wheat plants are incubated for 72 hours at about 18° C., under a humid atmosphere, and then for 14 days at 90% relative humidity.

Grading is carried out 15 to 20 days after contamination, in comparison with the control plants. Under these conditions, good (at least 50%) or total protection is observed, at a dose of 500 g/ha, with the following compounds: 1-2,2-5, 2 -6, 2-7, 2-8, 2-9, 2-12, 2-13, 2-19, 2-20, 2-21, 2-23, 2-24, 2-25, 2-26, 2-28, 2-32, 2-33, 2-34, 2-35, 2-36, 2-37, 2-38, 2-40, 2-41, 2-42, 2-43, 2-46, 2-47, 2-70, 2-71, 2-72, 2-76, 2-78, 2-84, 2-85, 2-93, 2-96

Example C

In Vivo Test on *Erysiphe graminis* f. sp. tritici (Powdery Mildew of Wheat)

An aqueous suspension, at a concentration of 1.5%, of the active material tested is obtained by grinding it finely in a formulation of concentrated suspension type. This aqueous suspension is then diluted in water so as to obtain the desired active material concentration. Wheat plants (Audace variety) in starter cups, sown on 50/50 peat soil-pozzulana substrate and grown at 12° C., are treated at the 1-leaf stage (10 cm tall) by spraying with the aqueous suspension described above. Plants, used as controls, are treated with an aqueous solution not containing the active material. After 24 hours, the plants are contaminated by dusting them with *Erisyphe graminis* f. sp. *tritici* spores, the dusting being carried out using diseased plants.

Grading is carried out 7 to 14 days after the contamination, in comparison with the control plants. Under these conditions, good (at least 50%) or total protection is observed, at a dose of 500 g/ha, with the following compounds: 1-2, 1-3, 2-5, 2-6, 2-7,2-8, 2-9,2-12, 2-13, 2-14, 2-15, 2-17, 2-18; 2-19, 2-20, 2-21, 2-22, 2-23, 2-24, 2-25, 2-26, 2-42, 2-43, 2-44, 2-29, 2-31, 2-32, 2-33, 2-34, 2-35, 2-36, 2-37, 2-40, 2-41, 2-46, 2-47, 2-48, 2-49, 2-53, 2-68, 2-71, 2-76, 2-78, 2-79, 2-80, 2-83, 2-84, 2-85, 2-93, 2-96, 2-97.

Example D

In Vivo Test on *Septoria tritici* (Leaf Spot of Wheat)

An aqueous suspension, at a concentration of 1.5%, of the active material tested is obtained by grinding it finely in a formulation of concentrated suspension type. This aqueous suspension is then diluted in water so as to obtain the desired active material concentration. Wheat plants (Scipion variety) in starter cups, sown on a 50/50 peat soil-pozzolana substrate and grown at 12° C., are treated at the 1-leaf stage (10 cm tall) by spraying with the aqueous suspension described above. Plants, used as controls, are treated with an aqueous solution not containing the active material.

After 24 hours, the plants are contaminated by spraying them with an aqueous suspension of *Septoria tritici* spores (500,000 spores per mL). The spores are collected from a 15-day-old culture and are suspended in a nutrient solution composed of:

1.5 g/L of gelatine
0.5 g/L of sodium oleate
24 g/L of PDB

The contaminated wheat plants are incubated for 72 hours at about 20° C. and at 100% relative humidity, and then for 15 days at 80% relative humidity.

Grading is carried out 15 to 20 days after the contamination, in comparison with the control plants. Under these conditions, good (at least 50%) protection is observed, at a dose of 500 g/ha, with the following compounds: 1-2, 1-3, 2-5, 2-6, 2-7, 2-8, 2-12, 2-18, 2-19, 2-20, 2-21, 2-22, 2-23, 2-30, 2-31, 2-34, 2-40, 2-46, 2-47, 2-70, 2-71, 2-72, 2-74, 2-75, 2-76, 2-80, 2-83, 2-84, 2-85, 2-91, 2-93, 2-2-96, 2-98.

Example E

In Vivo Test on *Puccinia recondita* (Wheat Brown Rust)

An aqueous suspension, at a concentration of 1.5%, of the active material tested is obtained by grinding it finely in a formulation of concentrated suspension type, This aqueous suspension is then diluted in water so as to obtain the desired active material concentration. Wheat plants (Scipion variety) in starter cups, sown on a 50/50 peat soil-pozzolana substrate and grown at 12° C., are treated at the 1-leaf stage (10 cm tall) by spraying with the aqueous suspension described above. Plants, used as controls, are treated with an aqueous solution not containing the active material.

After 24 hours, the plants are contaminated by spraying them with an aqueous suspension of *Puccinia reconidita* spores (150,000 spores per mL). The contaminated wheat plants are incubated for 24 hours at about 20° C. and at 100% relative humidity, and then for 10 days at 70% relative humidity.

Grading is carried out 10 days after the contamination, in comparison with the control plants. Under these conditions, good (at least 50%) protection is observed, at a dose of 500 g/ha, with the following compounds described as example: 1-2, 2-5, 2-7, 2-9, 2-12, 2-13, 2-18, 2-22, 2-34, 2-46, 2-47, 2-69, 2-71, 2-76, 2-79, 2-80, 2-84, 2 -85, 2-94, 2-96, 2-98.

Example F

In Vivo Test on *Botrytis cinerea* (Cucumber Grey Mould)

An aqueous suspension, at a concentration of 1.5%, of the active material tested is obtained by grinding it finely in a formulation of concentrated suspension type. This aqueous suspension is then diluted in water so as to obtain the desired active material concentration. Cucumber plants (Marketer variety) in starter cups, sown on a 50/50 peat soil-pozzolana substrate and grown at 18–20° C., are treated at the cotyledon Z11 stage by spraying with the aqueous suspension described above. Plants, used as controls, are treated with an aqueous solution not containing the active material.

After 24 hours, the plants are contaminated by depositing drops of an aqueous suspension of *Botrytis cinerea* spores (150,000 spores per ml) on upper surface of the leaves. The spores are collected from a 15-day-old culture and are suspended in a nutrient solution composed of:

20 g/L of gelatine
50 g/L of cane sugar
2 g/L of NH4NO3
1 g/L of KH2PO4

The contaminated cucumber plants are settled for 5/7 days in a climatic room at 15–11° C. (day/night) and at 80% relative humidity.

Grading is carried out 5/7 days after the contamination, in comparison with the control plants. Under these conditions, good (at least 50%) protection is observed, at a dose of 500 g/ha, with the following compounds described as example: 2-11, 2-20, 2-70, 2-91, 2-92, 2-94, 2-96, 2-98.

What is claimed is:

1. A compound of the formula (I):

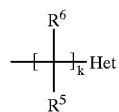

(I)

wherein:

Y is

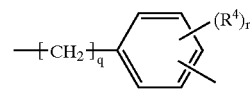

k is 0, 1, or 2;

Het is a five- or six-membered saturated or partially unsaturated, or aromatic ring comprising from one to three heteroatoms independently selected from the group consisting of N, O, and S and which can be substituted with one or two —$R^5$ groups;

G is selected from the group consisting of —O—, —S—, and —$NR^1$;

Z is —$R^1$;

$X^1$ and $X^2$ are independently selected from the group consisting of hydrogen, halogen, —$CE_3$, cyano, and nitro;

$Q^1$ is

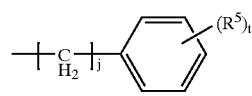

$Q^2$ is —$(O)_n$—$R^9$;

$R^1$ is hydrogen or $C_1$–$C_4$ alkyl;

$R^2$ is selected from the group consisting of hydrogen, halogen, $C_1$–$C_4$ alkyl, $C_1$–$C_4$ alkoxy, $C_1$–$C_4$ halogenoalkyl, and $C_1$–$C_4$ halogenoalkoxy;

$R^3$ is selected from the group consisting of hydrogen, $C_1$–$C_4$ alkyl, and $_1$–$C_4$ alkoxyalkyl;

$R^4$ is selected from the group consisting of halogen, $C_1$–$C_4$ alkyl, and $C_{1-C4}$ alkoxyalkyl;

$R^5$ and $R^6$ are independently selected from the group consisting of hydrogen, halogen, $C_1$–$C_4$ alkyl, and $C_1$–$C_4$ halogenoalkyl;

$R^7$ and $R^8$ are independently selected from the group consisting of hydrogen and halogen;

$R^9$ is $R^5$ or

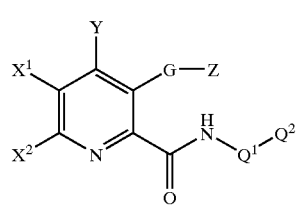

n is 0 or 1;

j, q, and t are independently 0, 1, 2, 3, or 4;

and the optional N-oxides, geometric and/or optical isomers, enantiomers and/or diastereoisomers, tautomeric forms, salts, metal and metalloid complexes of the compounds of formula (I) as they have just been defined.

2. A process for the preparation of a compound of the formula (I)

(I)

wherein

Y, $X^1$, $X^2$G, Z, $Q^1$, and $Q^2$ are as defined in claim 1, k=0, and the Het group is directly linked to the rest of the structure by a nitrogen atom, comprising reacting a compound of the formula (IIIa) according to scheme S-II:

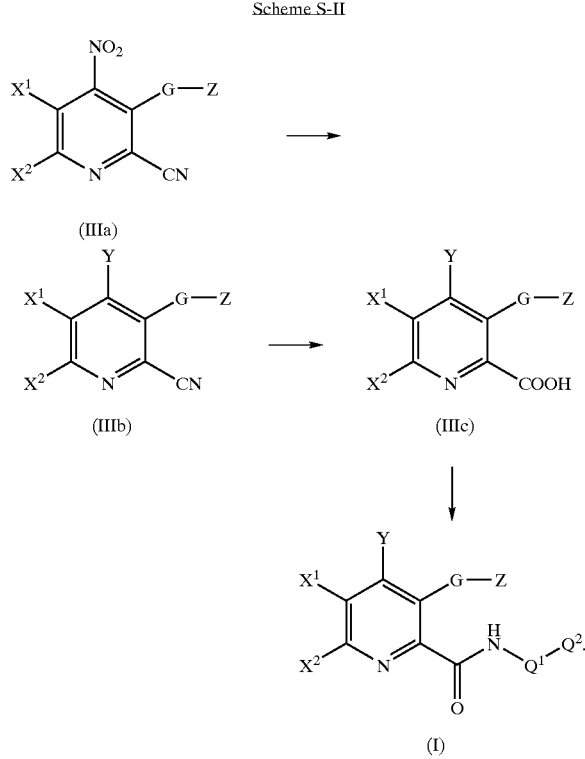

Scheme S-II

3. The compound of claim 1 wherein Y is selected from the group consisting of pyrroles, dimethylpyrroles and imidazole.

4. The compound of claim 1 wherein G is —O—.

5. A fungicidal composition comprising an effective amount of the compound of claim 1 and an agriculturally acceptable support.

6. The fungicidal composition of claim 5 further comprising a surfactant.

7. The fungicidal composition of claim 5 comprising from 0.05% to 99% by weight of active material.

8. The fungicidal composition of claim 6, comprising from 0.05% to 99% by weight of active material.

9. A method for preventively or curatively combating the phytopathogenic fungi of crops comprising applying an effective and non-phytotoxic amount of the fungicidal composition of claim 5 to the plant seeds or to the plant leaves and/or to the fruits of the plants or to the soil in which the plants are growing or in which it is desired to grow them.

10. The method of claim 9 wherein the dose of active material applied is between 10 g and 800 g of active material per hectare in the case of foliar treatments.

11. The method of claim 10 wherein the dose of active material applied is between 50 g and 300 g of active material per hectare in the case of foliar treatments.

12. The method of claim 9 wherein the dose of active material applied is between 2 and 200 g of active material per 100 kg of seed, in the case of seed treatments.

13. The method of claim 12 wherein the dose of active material applied is between 3 g and 150 g per 100 kg of seed, in the case of seed treatments.

* * * * *